United States Patent
Taneja et al.

(10) Patent No.: US 6,787,674 B1
(45) Date of Patent: Sep. 7, 2004

(54) (+)-1-BISABOLONE ISOLATED FROM *CYMBOPOGON FLEXUOSUS* AND ANTIBACTERIAL ACTIVITY THEREOF

(75) Inventors: Subhash Chandra Taneja, Jammu (IN); Ashok Kumar Shahi, Jammu (IN); Vijeshwar Verma, Jammu (IN); Vijay Kumar Sethi, Jammu (IN); Samar Singh Andotra, Jammu (IN); Abid Zaffar Hashmi, Jammu (IN); Prabhu Dutt, Jammu (IN); Sanotosh Kumar Bakshi, Jammu (IN); Maharaj Krishan Koul, Jammu (IN); Satya Narayan Sharma, Jammu (IN); Suresh Chandra, Jammu (IN); Ghulam Nabi Qazi, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/401,128

(22) Filed: Mar. 27, 2003

(51) Int. Cl.[7] .......................... C07C 45/00; C07C 49/00; C11B 1/00
(52) U.S. Cl. ............................ 568/366; 568/377; 554/8
(58) Field of Search ................................ 568/366, 377; 554/8

(56) References Cited

FOREIGN PATENT DOCUMENTS

GB          2359746         9/2001

OTHER PUBLICATIONS

Hagiwara et al. Catalytic enamine reaction: an expedient 1,4–conjugate addition of naked aldehydes to vinylketones and its application to synthesis of cyclohexenone from Stevia pururea. Tetrahedron Letters (2001), 42 (14) p 2705–2707.*

Morris, J.A. et al. "Antimicrobial Activity if Aroma Chemicals and Essential Oils" Journal of the American Oil Chemists' Society, vol. 56, (May, 1979) p. 595–603.

Hagiwara, Hisahiro, et al. "Total synthesis of bisabolane sesquiterpenoids, α–bisabol–1–one, curcumene, curcuphenol and elvirol: utility of catalytic enamine reaction in cyclohexenone synthesis" J. Chem. Soc., Perkin Trans. 1, 2002, p. 895–900.

Abegaz, Berhanu, et al. "Constituents Of The Essential Oil Of Ethiopian *Cymbopogan Citratus* Stapf" Journal of Natural Products, vol. 46, No. 3 (May–Jun. 1983) p. 424–426.

* cited by examiner

*Primary Examiner*—Johann Richter
*Assistant Examiner*—Sikarl A. Witherspoon
(74) *Attorney, Agent, or Firm*—Ladas & Parry

(57) ABSTRACT

The present invention relates to anti-microbial activity of the essential oil of *Cymbopogon flexuosus* (Nees ex Steud) Wats and the process of isolation of novel sesquiterpene compound which is mainly responsible for the strong anti-microbial/anti-bacterial activity. The present invention particularly relates to anti-bacterial activity of the essential oil and a pure isolate identified as (+)-1-bisabolone of formula 1 against gram positive bacteria from a strain of a grass identified as *Cymbopogon flexuosus*.

9 Claims, No Drawings

(+)-1-BISABOLONE ISOLATED FROM *CYMBOPOGON FLEXUOSUS* AND ANTIBACTERIAL ACTIVITY THEREOF

FIELD OF THE INVENTION

The present invention relates to anti-microbial activity of the essential oil of *Cymbopogon flexuosus* (Nees ex Steud.) Wats and the process of isolation of novel sesquiterpene compound mainly responsible for the strong anti-microbial/anti-bacterial activity. The present invention particularly relates to anti-bacterial activity of the essential oil and a pure isolate identified as (+)-1-bisabolone of formula 1 against gram positive bacteria from a strain of a grass identified as *Cymbopogon flexuosus*.

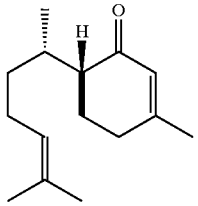

Formula 1

BACKGROUND OF THE INVENTION

*Cymbopgon species* (family Poaceae) arc native to tropical and subtropical regions of Asia and Africa. The aromatic grasses such as Cymbopogon and *Vetiveria zizanioides* have been known because of their medicinal and perfumery values. The genus Cymbopogon is well known source of aroma chemicals especially terpenoids. Essential oil derived from Cymbopogon species such as Java citronella (*Cymbopogon winterianus*), Palmarosa (*Cymbopogon martini* var. *motia*) and Lemongrass (*Cymbopogon flexuosus*) are very popular and widely consumed in the world market. The chemical compounds present in varying concentrations in the species, varieties, ecotypes and chemotypes of the Cymbopogon grass have a great demand due to their uses in perfumery, flavour and pharmaceutical industry. There are approximately sixty species of Cymbopogon native to tropical and subtropical regions of Africa and Asia. (Corrigan, D 1992, in "Adverse Effects of Herbal Drugs" Vol. 1, Springer verlag, Berlin, 115–123). Out of twenty seven species available in India mainly *Cymbopogon flexuosus, C.winterianus* and *C.martini* var. *motia* have been exploited for commercial cultivation as a source of citral, citronellal and geraniol respectively.

Development of the new chemocultivars having the higher percentage of essential oils is generally carried out by the method of phenotypic mass selection. The oil obtained from the elite stain of *Cymbopogon flexuosus*, described herein, RLJCF (HSR) is rich in (+)-1-bisabolone of formula 1 (30–50%) which owing to strong UV absorption at 224 nm and refreshing flowery note including potent anti-bacterial properties may find extensive use in sun-screen lotions, creams and related preparations as well as in the antiseptic and deodorizing preparations such as creams, after shave lotions, sprays and powders.

There are a few reports of the occurrence of (−)-1-bisabolone from a natural source. The first report of its presence (15%) in *Stevia purpurea* Pers was made by F. Bohlmann et al. (F. Bohlmann, C. Zedro and S. Schonewiess, *Chem. Ber.* 109, 1976, 3366–3370). Another publication reporting its presence (12%) in Ethopian *Cymbopogon citratus*. (B. Abegaz, P. G. Yohaunes and R. K. Dieter, *Jour. Nat. Prod.* 46, 1983, 424–426). Melkani et al. also reported the enantiomer (−)-1-bisabolone in concentration ranging from 18–68% In one of the oils of two varieties of *Cymbopogon distans* (A. B. Melkani, P. Joshi, A. K. Pant, C. S. Mathela and Vasudev, *Jour. Nat. Prod.* 48, 1985, 995–997).

OBJECTS OF THE INVENTION

The main object of the present invention is to unravel the potent anti-bacterial activity of main constiutent (+)-1-bisabolone preset in the volatile oil of the locally developed and grown plant *Cymbopogon flexuosus*, named RLJCF (HSR).

SUMMARY OF THE INVENTION

From a detailed scrutiny of the published literature it is apparent that the presence of (+)-1-bisabolone from a natural source has not been reported earlier. Therefore, the presence of (+)-1-bisabolone from *Cymbopogon flexuosus* being the first report, is novel and the anti-bacterial activity of the oil bearing the active compound is also novel.

Accordingly the present invention relates to a novel sesquiterpene, (+)-1-bisabolone of the formula 1 given below

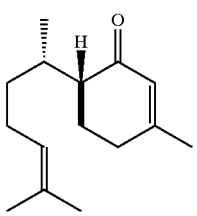

Formula 1

The present invention also relates to a process for the isolation of a novel sesquiterpene, (+)-1-bisabolone of the formula 1 from *Cymbopogon flexuosus*

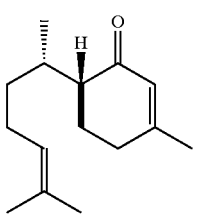

Formula 1 said process comprising hydrodistilling freshly harvested leaves of the grass *Cymbopogon flexuosus*, extracting the distillate with a non-polar solvent to obtain a concentrate, further hydrodistilling the obtained concentrate and separating the essential oil, followed by separating of the sesquiterpene of formula 1 from the essential oil.

In one embodiment of the invention, the non-polar solvent used for extraction of the distillate is selected from the group consisting of n-hexane, petroleum ether and dichloromethane.

In one embodiment of the invention, the sesquiterpene of the formula 1 is separated from the essential oil using column chromatography.

In yet another embodiment of the invention, the yield of (+)-1-bisabolone of formula 1 from *Cymbopogon flexuosus* essential oil is 35–45%.

In another embodiment of the invention, the (+)-1-bisabolone of formula 1 possesses in vitro anti-microbial activity against gram positive bacteria selected from *Bacillus cereus, Staphylococcus aureus* and *Bacillus subtilis.*

In another embodiment of the invention, the sesquiterpene of the formula 1 is separated from the essential oil using fractionation.

The present invention also relates to an essential oil obtained form the freshly harvested leaves of *Cymbopogon flexuosus* and containing a sesquiterpene (+)-1-bisabolone as the active ingredient, said essential oil being anti-bacterial activity against gram positive bacteria.

In another embodiment of the invention, the yield of (+)-1-bisabolone rich oil from *Cymbopogon flexuosus* is 0.3–0.4%.

In another embodiment of the invention, the essential oil possesses in vitro anti-microbial activity against gram-positive bacteria selected from *Bacillus cereus, Staphylococcus aureus* and *Bacillus subtilis.*

DETAILED DESCRIPTION OF THE INVENTION

The methodology adopted comprises following steps:
a) Chopping of the freshly harvested leaves of the grass *Cymbopogon flexuosus* [RLJCF(HSR)].
b) Hydrodistillation of the plant material in a Clevenger type distillation unit or extraction of the material with non polar solvent such as n-hexane, petroleum ether, dichloromethane and the like and hydrodistillation of the concentrate and separation of the essential oil from the aqueous part.
c) Separation of the sesquiterpene of formula 1 from the essential oil by column chromatography or by fractional distillation. In vitro anti-bacterial activity of the essential oil and the pure isolate (+)-1-bisabolone.

In the preferred embodiment of the invention is described the isolation of the novel sesquiterpene (+)-1-bisabolone of formula 1 displaying potent anti-bacterial activity against gram positive bacteria The method comprises,
a) Chopping of the freshly collected leaves of the plant *Cymbopogon flexuosus* by known methods.
b) Separation of the volatile oil of the plant in the Clevenger type apparatus by extraction with a non-polar solvent such as hexane, petroleum ether, dichloromethane and the like followed by concentration and hydrodistillation or direct hydrodistillation in an amount of 0.3–0.4% calculated on the basis of wet plant.
c) Isolation and separation of the compound(+1-bisabolone of formula 1 in 35–50% of the total oil by column chromatography or by factional distillation method.
d) In vitro antibacterial activity of novel sesquiterpene (+)-1-bisabolone of formula 1 particularly against gram positive bacteria particularly against *Bascillus cereus* and *Staphylococcus aureus* of bacteria.

The following methodology was employed for the development of the present strain having novel chemical attributes in its essential oil.

The germplasm of *Cymbopogon flexuosus* (Nees es Steud.) Wats was collected from wild habitats near Haryanas-Rajasthan border and planted in the experimental farm at Regional Research Laboratory, Jammu for morphological and chemical characterisation. During the screening programme of the population raised in our experimental plots one of the plants was found to have very interesting chemical composition. This genotype was vegetatively propagated, and named RLJCF (HSR). It has been grown as sizeable plantation at farm of RRL, Jammu.

The essential oil of *Cymbopogon flexuosus* was obtained by hydrodistillation method using Clevenger type distillation apparatus. Triplicate distillations were performed in succession from each sample of 500 g of freshly chopped leaves. The oil obtained was dried over anhydrous sodium sulphate and subjected to the isolation of the (+)-1-bisabolone of formula 1 by column chromatography method and by fractional distillation. On detailed in vitro studies of the novel sesquiterpene isolate (+)-1-bisabolone of formula 1 it was found to have excellent activity against many test bacterial. The oil as well as the compound has been found strongly active against *Bacillus cereus, Staphylococcus aures, Bacillus subtilis* and good to moderate activity against other test bacteria. Experimentally (+)-1-bisabolone of formula 1 has shown comparatively far better activity than the standard ampicillin used for gram positive bacteria.

Accordingly the present invention provides anti-bacterial activity against gram positive bacteria of the novel and main constituent (+)-1-bisabolone of formula 1 isolated from the essential oil of *Cymbopogon flexuosus*, which comprises
a) Chopping of the fresh leaves of the plant by known methods.
b) Separation of the volatile oil of the plant in the Clevenger type apparatus by known methods.
c) Isolation and separation of the compound (+)-1-bisabolone of formula 1.
d) In vitro anti-bacterial activity of the novel sesquiterpene (+)-1-bisabolone of formula 1 against gram positive bacteria.

The invention is ether illustrated by the following non-limiting examples:

EXAMPLE-1 a) Freshly collected and finely chopped plant material of a chemotype of *Cymbopogon flexuosus* (500 g), developed through phenotypic mass selection technique by our laboratory and grown and domesticated in institutional farm was subjected to hydro-distillation using Clevenger type apparatus to isolate the volatile oil. Boiling of the aqueous mixture continued exhaustively for three hours till approximately 3 ml (0.6%) of pale yellow coloured oil was collected.

The oil (d, 0.92) has a typical green flowery odour. GLC of the oil on column showed approximately twenty different peaks, of which one is major (35–45%). List of some of the volatile components identified by GC/MS analysts is presented in Table-1 b) 5 g of the separated oil was subjected to column chromatography over silica gel (250 g) using hexane ethyl acetate (20:1–5:1). The fractions eluted with hexanen-:ethyl acetate (10:1) on removal of the solvent furnished light yellow liquid (1.9 g) with typical green flowery odour. The compound was identified as (+)-1-bisabolone of formula 1 by its spectral data which is presented as under.

The isolated pure product has $[\alpha]_D$ (+)−26°(neat) and (+)−16° (CHCl$_3$, 4,c). $^1$HNMR(CDCl$_3$) δ:0.83(3H, d, J=6 Hz, CH$_3$), 1.26(4H, bs, CH$_2$), 1.59 & 1.69 (2×3H, 2×s, 2×CH$_3$), 5.16(1H, t, J=6.5 Hz, =CH), 5.89(1H, s, =CH). $^{13}$CNMR(CDCl$_3$):15.63, 22.45, 24.12, 26.05, 26.23, 30.33, 30.55, 30.97, 34.79, 49.91, 124.59, 126.92, 131.37, 161.12, 201.03.

EXAMPLE-2

Freshly collected and finely chopped plant material of a chemotype of *Cymbopogon flexuosus* (500 g), was subjected to Soxhlet extraction with n-hexane (3 lt) for 12 hours till the completion of the extraction. The hexane extract was then concentrated on thin film evaporator under reduced pressure to furnish a thick greenish yellow colour liquid (42 g). 5 g of this liquid was subjected to column chromatography over silica gel (300 g). Elution with hexane:ethyl acetate (20:1–5;1). The fractions eluted with hexane:ethyl acetate (10;1) on removal of the solvent furnished light yellow liquid (2.4 g) with typical green flowery odour. The compound was identified as (+)-1-bisabolone of formula 1 by its spectral data.

EXAMPLE-3

Freshly collected and finely chopped plant material of a chemotype of Cymbopogon flexuosus (1 kg), developed through phenotypic mass selection process by our laboratory was subjected to hydro-distillation using the Clevenger type apparatus to isolate the volatile oil. Boiling of the aqueous mixture continued exhaustively for three hours till approximately 3.9 ml (0.39%) of pale yellow colour oil was collected. The oil was subjected to fraction distillation under reduced pressure (5.0–50 mm) through a fractional distillation column at a temperature range of 90° C. to 160° C. The initial lower boiling fractions rich in hydrocarbons and monoterpenes were discarded. The factions which came last at 150,° C.–160° C. (5–10 mm) were combined to produce pale yellow fraction containing 85–90% of 1-bisabolone (GLC), total yield 35% of the oil.

EXAMPLE-4

Anti-bacterial Activity of (+)-1-Bisabolone of Formula 1

The pure bacterial cultures of test bacteria were procured from laboratory culture collection maintained at RRL, Jammu. The bacterial organisms were subcultured on L B. broth. Following filter paper disc agar diffusion method (Maruzella, J. C. and Henry, P. A. 1958, the antifungal activity of perfume oils. *J. Amer. Pharm. Ass.*, 47:471–476).

20 ml of sterilized medium was taken in each petriplate. After the agar has hardened, 2 ml of 24 hrs. broth culture of organism was added to each petriplate and mixed thoroughly by rotatory motion of the plate and allowed to set. The sterilized Whatman filter paper No. 1 discs (4 mm diameter) were thoroughly moistened with 5 μl of (+)-1-bisabolone of formula 1 in dilution of 1:50, 1:100 in the solvent Tween-80 and placed on the seeded agar plates. The standard antibiotic disc of ampicillin was placed on surface of each seeded petriplate as standard for anti-bacterial activity. Three each of seeded agar plates for each organism were incubated at 37° C. for 36 hrs. The relative susceptibility of the organism to the compound of formula 1 was demonstrated by a clear zone of inhibition around the disc. The zone of inhibition was measured with the help of a divider. The exponents were performed in triplicate and average zones of inhibition for anti-bacterial activity are recorded in Table-2.

TABLE 1

Chemical constituents of C. flexuosus RLJCF (HSR)*

| Chemical constituents | Percentage |
| --- | --- |
| 1-Bisabolone | 45.28 |
| Limonene | 7.14 |
| Geraniol | 6.00 |
| Camphene | 4.38 |

TABLE 1-continued

Chemical constituents of C. flexuosus RLJCF (HSR)*

| Chemical constituents | Percentage |
| --- | --- |
| Car-2-ene | 3.59 |
| β-elemene | 3.42 |
| Borneol | 3.34 |
| Citronellol | 2.89 |
| Piperitone | 2.43 |
| Citronellal | 2.31 |
| Caryophyllene | 1.66 |
| α-pinene | 1.49 |
| Terpineol | 1.31 |
| Neral | 1.23 |
| Geranial | 1.13 |
| Unidentified | 16.00 |

TABLE 2

In vitro antibacterial activity of (+)-1-bisabolone of formula 1

| | | Diameter (mm) of zone inhibition | | | |
| --- | --- | --- | --- | --- | --- |
| S.No. | Microorganism | Pure 1 | 1:50 | 1:100 | control |
| 1 | Bacillus cereus | 21 | 13 | 9 | 4 |
| 2 | Staphylococcus aureus | 24 | 19 | 13 | 6 |
| 3 | Bacillus subtilis | 19 | 15 | 13 | 5 |

We claim:
1. A process for the isolation of a sesquiterpene, (+)-1-bisabolone of the formula 1 from *Cymbopogon flexuosus*

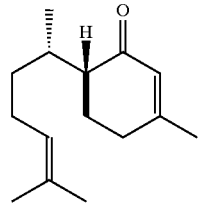

Formula 1 said process comprising the steps of:
 a) hydrodistilling freshly harvested leaves of the grass *Cymbopogon flexuosus*,
 b) extracting the distillate with a non-polar solvent to obtain a concentrate,
 c) further hydrodistilling the concentrate and separating the essential oil, followed by separating of the sesquiterpene of formula 1 from the essential oil.

2. The process as claimed in claim 1 wherein the non-polar solvent used for extraction of the distillate is selected from the group consisting of n-hexane, petroleum ether and dichloromethane.

3. The process as claimed in claim 1 wherein the sesquiterpene of the formula 1 is separated from the essential oil using column chromatography.

4. The process as claimed in claim 1 wherein the yield of (+)-1-bisabolone of formula 1 from *Cymbopogon flexuosus* essential oil is 35–45%.

5. The process as claimed in claim 1 wherein the (+)-1-bisabolone of formula 1 possesses in vitro anti-microbial activity against gram positive bacteria selected from the group consisting of *Bacillus cereus, Staphylococcus aureus* and *Bacillus subtilis*.

6. The process as claimed in claim 1 wherein the sesquiterpene of the formula 1 is separated from the essential oil using fractionation.

7. An essential oil obtained from the freshly harvested leaves of *Cymbopogon flexuosus* comprising a sesquiterpene (+)-1-bisabolone as the active ingredient, said essential oil having anti-bacterial activity against gram positive bacteria.

8. The essential oil as claimed in claim 7 wherein the yield of (+)-1-bisabolone containing essential oil from *Cymbopogon flexuosus* is 0.3–0.4%.

9. The essential oil as claimed in claim 7 wherein the essential oil possesses in vitro anti-microbial activity against gram-positive bacteria selected from the group consisting of *Bacillus cereus, Staphylococcus aureus* and *Bacillus subtilis*.

* * * * *